United States Patent
King et al.

(10) Patent No.: US 9,417,181 B2
(45) Date of Patent: Aug. 16, 2016

(54) DYNAMIC MEASUREMENT OF DENSITY USING TERAHERTZ RADIATION WITH REAL-TIME THICKNESS MEASUREMENT FOR PROCESS CONTROL

(71) Applicant: Advantest Corporation, Tokyo (JP)

(72) Inventors: Edward King, Dayton, OH (US); David Heaps, Yardley, PA (US); Mark Sullivan, Framingham, MA (US)

(73) Assignee: ADVANTEST CORPORATION, Tokyo (JP)

( * ) Notice: Subject to any disclaimer, the term of this patent is extended or adjusted under 35 U.S.C. 154(b) by 0 days.

(21) Appl. No.: 14/273,252

(22) Filed: May 8, 2014

(65) Prior Publication Data

US 2015/0323451 A1    Nov. 12, 2015

(51) Int. Cl.
*G01N 21/3563* (2014.01)
*G01N 21/3581* (2014.01)
*G01N 21/3586* (2014.01)
(Continued)

(52) U.S. Cl.
CPC ........ *G01N 21/3586* (2013.01); *G01B 11/0691* (2013.01); *G01N 21/3563* (2013.01); *G01N 21/85* (2013.01); *G01N 21/8901* (2013.01); *G01N 21/8914* (2013.01); *G01N 9/24* (2013.01); *G01N 21/3581* (2013.01);
(Continued)

(58) Field of Classification Search
CPC ..... G01N 21/86; G01N 21/89; G01N 21/892; G01N 21/898; G01N 21/3581; G01N 21/3586; G01N 21/3563; G01N 2021/3572; G01N 2021/06113; G01B 11/30; G01B 11/02; G01B 11/06; G01B 15/02; G01B 11/0691

USPC .......................... 356/429, 430, 431, 637, 630
See application file for complete search history.

(56) References Cited

U.S. PATENT DOCUMENTS

| 3,800,940 A | 4/1974 | Thomas |
| 5,973,316 A | 10/1999 | Ebbesen et al. |

(Continued)

FOREIGN PATENT DOCUMENTS

| EP | 2031374 A2 | 3/2009 |
| JP | 11-072607 | 3/1999 |

(Continued)

OTHER PUBLICATIONS

Ende, David, Chemical Engineering in the Pharmaceutical Industry: R & D to manufacturing, Mar. 10, 2011, Wiley, pages provided.*

(Continued)

*Primary Examiner* — Michael P Lapage

(57) ABSTRACT

A method of determining a density of a roller compacted ribbon is disclosed. The method comprises compacting dry pharmaceutical powder between press rollers of a roller compactor to produce a compact ribbon. The method also comprises determining a thickness at a point on the compact ribbon in a non-invasive manner after it has rolled out from in between the press rollers. Further, the method comprises passing the compact ribbon through a gap in between the terahertz emitter and the terahertz detector. Next, the method comprises determining a refractive index at the point on the compact ribbon using a measurement value from the terahertz emitter and the terahertz detector and a measured value for the thickness at the point. Finally, the method comprises computing a density of the compact ribbon at the point using a value of the refractive index.

20 Claims, 8 Drawing Sheets

(51) Int. Cl.
*G01B 11/06* (2006.01)
*G01N 21/85* (2006.01)
*G01N 21/89* (2006.01)
G01N 21/95 (2006.01)
G01N 9/24 (2006.01)

(52) U.S. Cl.
CPC ... *G01N 21/9508* (2013.01); *G01N 2021/3572* (2013.01); *G01N 2201/06113* (2013.01)

(56) References Cited

U.S. PATENT DOCUMENTS

| | | | |
|---|---|---|---|
| 6,052,238 | A | 4/2000 | Ebbesen et al. |
| 6,078,047 | A | 6/2000 | Mittleman et al. |
| 6,443,307 | B1 | 9/2002 | Burridge |
| 7,498,577 | B2 | 3/2009 | Kurosaka et al. |
| 7,551,269 | B2 | 6/2009 | Itsuji |
| 7,649,633 | B2 | 1/2010 | Kawate |
| 7,683,325 | B2 | 3/2010 | Sekiguchi et al. |
| 7,781,736 | B2 | 8/2010 | Logan, Jr. et al. |
| 7,795,582 | B2 | 9/2010 | Jez et al. |
| 8,271,128 | B1 | 9/2012 | Schultz |
| 8,712,163 | B1 | 4/2014 | Osheroff |
| 2003/0021734 | A1 | 1/2003 | Vann et al. |
| 2003/0063123 | A1 | 4/2003 | Fukube et al. |
| 2003/0063487 | A1 | 4/2003 | Steckl et al. |
| 2003/0152194 | A1 | 8/2003 | Nordmeyer et al. |
| 2003/0198619 | A1 | 10/2003 | Dong et al. |
| 2004/0061055 | A1 | 4/2004 | Kawase et al. |
| 2004/0241748 | A1 | 12/2004 | Ault-Riche et al. |
| 2005/0075335 | A1 | 4/2005 | Buxton et al. |
| 2005/0098728 | A1 | 5/2005 | Alfano et al. |
| 2005/0173637 | A1 | 8/2005 | Abrahamson et al. |
| 2005/0216075 | A1 | 9/2005 | Wang et al. |
| 2005/0253071 | A1 | 11/2005 | Ferguson et al. |
| 2006/0000470 | A1 | 1/2006 | Clarke et al. |
| 2006/0029941 | A1 | 2/2006 | Koo et al. |
| 2006/0043298 | A1 | 3/2006 | Kawase et al. |
| 2006/0045807 | A1* | 3/2006 | Zhang ............ G01N 33/54373 422/82.05 |
| 2006/0054824 | A1 | 3/2006 | Federici et al. |
| 2006/0228897 | A1 | 10/2006 | Timans |
| 2006/0237650 | A1 | 10/2006 | Taday |
| 2007/0138392 | A1* | 6/2007 | Cole .................. G01N 21/49 250/341.1 |
| 2007/0222693 | A1 | 9/2007 | Popa-Simil |
| 2007/0229094 | A1 | 10/2007 | Kasai et al. |
| 2007/0257216 | A1 | 11/2007 | Withers et al. |
| 2008/0239317 | A1 | 10/2008 | Schulkin et al. |
| 2009/0128799 | A1* | 5/2009 | MacHattie ........... D21G 9/0036 356/5.05 |
| 2010/0024999 | A1* | 2/2010 | Haran .................. D21F 7/003 162/198 |
| 2010/0066639 | A1 | 3/2010 | Ngyuen et al. |
| 2010/0102256 | A1 | 4/2010 | Andrew et al. |
| 2010/0108889 | A1 | 5/2010 | Shen et al. |
| 2010/0148070 | A1* | 6/2010 | Ho .................... G01N 21/3581 250/341.8 |
| 2012/0037804 | A1* | 2/2012 | Federici ............ G01N 21/3586 250/341.1 |
| 2012/0225475 | A1 | 9/2012 | Wagner et al. |
| 2012/0304756 | A1* | 12/2012 | White ............... G01N 21/3586 73/150 A |
| 2013/0075699 | A1 | 3/2013 | Brown et al. |
| 2013/0153767 | A1 | 6/2013 | Savoy et al. |
| 2013/0204577 | A1* | 8/2013 | Savard ............. G01B 11/0625 702/172 |
| 2013/0221082 | A1 | 8/2013 | Botten |
| 2013/0270596 | A1 | 10/2013 | Senellart et al. |
| 2014/0252231 | A1 | 9/2014 | Tomioka et al. |

FOREIGN PATENT DOCUMENTS

| | | |
|---|---|---|
| JP | 2004-108905 | 4/2004 |
| JP | 2004-117703 | 4/2004 |
| JP | 2007010366 | 1/2007 |
| WO | 2009156468 A1 | 12/2009 |

OTHER PUBLICATIONS

Acevedo, David, Evaluation of Three Approaches for Real-Time Monitoring of Roller Compaction with Near-Infrared Spectroscopy, Jul. 24, 2012, AAPS PharmSciTech, vol. 13, pp. 1005-1012.*
International Search Report (ISR) for PCT/JP2008/051404 for Examiner Consideration, Citing US Patent Application Nos. 1-2 and Foreign Patent Document Nos. 1-2 Listed Above.
Japanese Office Action dated Apr. 3, 2012, in a counterpart Japanese patent application No. 2007-021660. (Cited references have been submitted in a previous IDS).
Japanese Office Action dated Sep. 20, 2011, in a counterpart Japanese patent application No. 2001-021660, citing JP 2007-010366, JP H11-072607 and Lamarre et al., "Metallic Mesh Properties and Design of Submillimeter Filters", Ogawa et al., "Usugata Kinzoku Mesh no Toka Tokusei O Riyo shita Sensor Oyo", and Ogawa et aL, "Printable Mesh O Mochiita Terahertz-tai Kussetsuritsu Sensor", which have been submitted in a previous IDS. A machine translation (not reviewed for accuracy) attached.
Lamarre et al., "Metallic Mesh Properties and Design of Submillimeter Filters", International Journal of Infrared and Millimeter Waves, vol. 2, 1981, pp. 273-292. Cited in ISR and mentioned on p. 2 of as-filed specification.
May, R. K., et al., "Terahertz in-line sensor for direct coating thickness measurement of individual tablets during film coating in real-time", 2011, J. Pharm. Sci., 100: 1535-1544.
Ogawa et aL, "Printable Mesh O Mochiita Terahertz-tai Kussetsuritsu Sensor", Dai 66 Kai Extended abstracts; the Japan Society of Applied Physics, Sep. 7, 2005, Dai 66 Kai, separate vol. 3, p. 966, 9a-P6-26. Cited in ISR as concise explanation of relevance.
Ogawa et aL, "Usugata Kinzoku Mesh no Toka Tokusei O Riyo shita Sensor Oyo", Dai 67 Kai Exended abstracts; The Japan Society of Applied Physics, Aug. 29, 2006, Dai 67 Kai, separate vol. 3, p. 1016, 31p-za-2. Cited in ISR as concise explanation of relevance.
Sakai, "Terahertz Time-Domain Spectroscopy" Spectroscopy Studies, Vol. 50, No. 6, pp. 261-273, 2001, Kobe, Japan. Mentioned on p. 1 of As-Filed Specification As Concise Explanation of Relevance.
Written Option (PCT/ISA/237) of PCT/JP2008/051404.
Yoshida et al., "Kinzoku Mesh ni yoru Tanpakushitsu no Label Free Kenshutsu", IEICE Technical Report, Nov. 20, 2007, vol. 107, No. 355, p. 99-102. Cited in ISR as concise explanation of relevance.
Yoshida et al., "Terahertz sensing method for protein detection using a thin metallic mesh", Applied Physics Letters, Dec. 17, 2007, vol. 91, No. 25, p. 253901-1-p. 253901-3. Cited in ISR.

* cited by examiner

DYNAMIC MEASUREMENT OF DENSITY USING TERAHERTZ RADIATION WITH REAL-TIME THICKNESS MEASUREMENT FOR PROCESS CONTROL

FIELD OF THE INVENTION

Embodiments according to the present invention generally relate to automated test equipment and, more specifically, to performing measurements using terahertz (THz) spectroscopy in automated test equipment.

BACKGROUND OF THE INVENTION

Automated test equipment (ATE) relates to any testing assembly that performs a test on a device or material under test. ATE assemblies may be used to execute automated tests that quickly perform measurements and generate test results that can then be analyzed. An ATE assembly may be anything from a computer system coupled to a meter, to a complicated automated test assembly that may include a custom, dedicated computer control system and many different test instruments that are capable of automatically testing electronics parts and/or performing measurements. ATE systems both reduce the amount of time spent on testing devices to ensure that the device or material functions as designed and serve as a diagnostic tool to determine the existence of any problems or complications before the device or material reaches the consumer.

For example, ATE can be used in the pharmaceutical industry to ensure that the dry granulation process was a success. Dry granulation is a pharmaceutical formulation process that produces mixed products without adding liquids. Forming granules without moisture requires compacting the powders. Dry granulation is a process in which the particles of a uniform powder mixture are forced to adhere to one another under pressure and then the resultant compact is milled into large particles that have desirable flow characteristics. When the powder blend is compacted by applying force to the powder, it results in considerable size enlargement. The resulting compact is referred to as a ribbon.

The bonding of materials together in the granules reduces the tendency of the components to segregate during processing, which in turn results in content uniformity in the final dosage form.

The two conventional ways of obtaining the compact using dry granulation is slugging or roller compaction. Slugging typically involves using tablet presses for the compaction process. Large tablets are produced in a heavy duty tableting press. However, because it is inefficient, it is rarely used. For example, the powders may not possess enough natural flow to feed the product uniformly, resulting in various degrees of density in the final product.

The preferred method for performing compaction for pharmaceuticals is roller compaction. Roller compaction comprises squeezing the powder between two rollers to produce a sheet of materials or a ribbon. At a given force, depending on the amount of powder conveyed to the rollers, the powder is compacted to a predefined ribbon thickness.

FIG. 1 illustrates an example of a conventional roller compactor (or chilsonator). A roller compactor typically comprises three major parts: a) a powder feeder comprising an inlet funnel with agitator 120, an inlet funnel 124, a feed auger 121 and a tamp auger 122; b) a compaction unit in which powder is compacted between two counter rotating press rollers 125 to a ribbon; and c) a size reduction unit comprising a rotor 126 in which the ribbon is milled to the desired particle size. The roller compactor uses an auger-feed system that will consistently deliver powder uniformly between the press rollers 125. The ribbon is then milled into granules in order to make a flowing powder that can be fed into the tablet press. Accordingly, the powders are compacted into a ribbon between the rollers 125 and milled through a low-shear mill.

Conventionally, there are two types of roller compactors, a fixed gap roller compactor and a variable gap roller compactor. Both consist of the three major parts described above, but differ in the way in which the smallest distance or gap between the rolls is realized. In a fixed gap roller compactor, the compaction force varies with the amount of powder that enters the rollers. By contrast, in the variable gap roller compactor the distance between the rollers changes with the amount of powder drawn into the compaction area to yield a constant force. The fixed gap roller compactor results in a ribbon with constant thickness and variable density while the variable gap roller compactor results in a ribbon with constant density and variable thickness.

Changes in ribbon density typically cause large fluctuations in granulate properties. In ribbon formulation, efforts are made to determine the uniformity and density of the ribbon because the ribbon mixture represents the component makeup of the pharmaceutical. Traditionally, the density of ribbons is measured using microindentation hardness testing. Microindentation hardness testing typically involves making a constant pressure dent in a designated location on different areas of the ribbon. Subsequently, the depth of the dent is measured using microscopy. This is a manual measurement that requires physically cutting the ribbon, denting the ribbon with the indentation device, and finally measuring the indentation with a microscope.

Microindentation hardness testing is not ideal because it is slow and invasive and, therefore, not suited for on-line testing. Because microindentation hardness testing is not an on-line method, the time period between the test and analysis to verify the density of the ribbon is long. This can lead to significant delays and a large amount of wasted product if the problem is detected too far into the process.

Micro X-ray computed tomography is a well-known spatially localized imaging technique that is used to measure the local density of a ribbon. However, similar to microindentation hardness testing, micro X-ray tomography is not well-suited to real-time online applications.

BRIEF SUMMARY OF THE INVENTION

Accordingly, a need exists for a tester system and/or method that can address the problems with the systems described above. What is needed is a faster, non-invasive and more efficient mechanism to measure the density of a ribbon produced by the roller compaction process. Further, what is needed is a method and apparatus to implement the test on/at-line so that the density of the ribbon can be measured in real-time as the ribbon is rolled out from in between the press rollers.

Using the beneficial aspects of the systems described, without their respective limitations, embodiments of the present invention provide novel solutions to the challenges inherent in testing for the density of ribbons produced by roller compactors during a dry granulation process.

In one embodiment, terahertz time-domain spectroscopy (THz-TDS) is used to measure the refractive index of the compact at one or more points on the ribbon after it is rolled out from the press rollers. In one embodiment, a terahertz (THz) emitter and detector can be placed on opposite sides of the ribbon to obtain measurements in transmission mode as the ribbon rolls out from in between the press rollers.

Variations in refractive index can be directly related (or directly proportional) to changes in density. In one embodiment, the density of the compact can, therefore, be determined provided that the sample thickness can be measured. In this embodiment, the present invention includes laser micrometers that take on-line measurements of the ribbon thickness. The laser micrometers can be mounted adjacent to the THz emitter and detector on opposite sides of the ribbon. By incorporating laser micrometers, microscopic changes in the thickness of the ribbon can be detected as the ribbon moves through the terahertz optical path. Accordingly, thickness measurements from the laser micrometers in conjunction with the measurements obtained from the terahertz spectroscopy can be used to calculate the refractive index of the ribbon material, which can, in turn, be used to determine the density of the pharmaceutical compact using a calibration equation.

In one embodiment, a method of determining a density of a roller compacted ribbon is presented. The method comprises compacting dry pharmaceutical powder between press rollers of a roller compactor to produce a compact ribbon. The method also comprises determining a thickness at a point on the compact ribbon in a non-invasive manner after it has rolled out from in between the press rollers. Further, the method comprises passing the compact ribbon through a gap in between the terahertz emitter and the terahertz detector. Next, the method comprises determining a refractive index at the point on the compact ribbon using a measurement value from the terahertz emitter and the terahertz detector and a measured value for the thickness at the point. Finally, the method comprises computing a density of the compact ribbon at the point using a value of the refractive index.

In another embodiment, an apparatus for determining a density of a roller compacted ribbon is presented. The apparatus comprises a roller compactor operable to compact dry pharmaceutical powder between press rollers of the roller compactor to produce a compact ribbon. The apparatus also comprises at least one laser micrometer operable to determine a thickness at a point on the compact ribbon in a non-invasive manner after it has rolled out from in between the press rollers. Further, the apparatus comprises a terahertz emitter operable to emit a terahertz radiation pulse through the point on the compact ribbon. Next, the apparatus comprises a terahertz detector operable to detect the terahertz radiation pulse. The apparatus also comprises a memory and a processor configured to: (a) determine a refractive index at the point on the compact ribbon using measured values from the terahertz emitter and the terahertz detector and a measured value for the thickness; and (b) compute a density of the compact ribbon at the point using a value of the refractive index.

In a different embodiment, a tester system is disclosed. The tester system comprises a roller compactor operable to compact dry pharmaceutical powder between press rollers of the roller compactor to produce a compact ribbon. The system also comprises a plurality of laser micrometer pairs operable to determine a thickness at a plurality of points on the compact ribbon in a non-invasive manner after it has rolled out from in between the press rollers, wherein the plurality of laser micrometer pairs are disposed adjacent to each other in a first axis direction in order to scan dedicated tracks along a ribbon flow in a second axis direction, and wherein each pair of laser micrometers is operable to determine a thickness at a single point from the plurality of points on the compact ribbon. The system also comprises a plurality of terahertz emitters, wherein each terahertz emitter is operable to emit a terahertz radiation pulse through a respective point from the plurality of points on the compact ribbon. Further, the system comprises a plurality of terahertz detectors, wherein each terahertz detector is operable to detect the terahertz radiation pulse passing through a respective point from the plurality of points on the compact ribbon. Finally, the system comprises a memory and a processor configured to: (a) determine a refractive index at each of the plurality of points on the compact ribbon using respective measured values from the terahertz emitter and the terahertz detector and a respective measured value for the thickness; and (b) compute a density of the compact ribbon at each of the plurality of points using a respective value of the refractive index.

The following detailed description together with the accompanying drawings will provide a better understanding of the nature and advantages of the present invention.

BRIEF DESCRIPTION OF THE DRAWINGS

Embodiments of the present invention are illustrated by way of example, and not by way of limitation, in the figures of the accompanying drawings and in which like reference numerals refer to similar elements.

Figure 1:
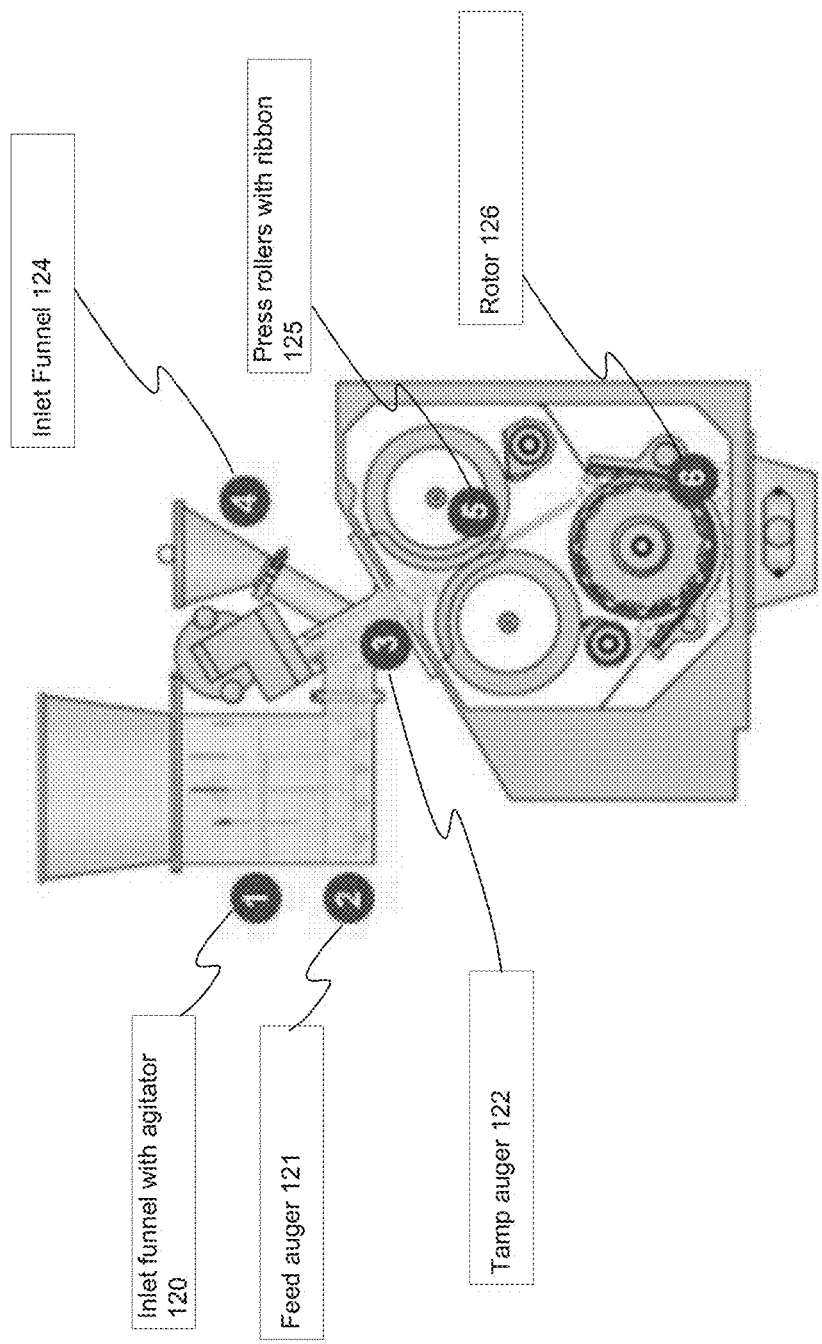
FIG. 1 illustrates an example of a conventional roller compactor.

In the figures, elements having the same designation have the same or similar function.

DETAILED DESCRIPTION OF THE INVENTION

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "configuring," "computing," "compacting," "passing," (e.g., flowchart 800 of FIG. 8) of a computer system or similar electronic computing device or processor. The computer system or similar electronic computing device manipulates and transforms data represented as physical (electronic) quantities within the computer system memories, registers or other such information storage, transmission or display devices.

Dynamic Measurement of Density Using Terahertz Radiation with Real-Time Thickness Measurement for Process Control The powder properties of pharmaceutical materials play an important role in determining the manufacturability and performance of solid dosage forms. For a product manufactured by dry granulation, the properties of the resultant granules can have a direct impact on downstream operations such as milling and tabletting, as well as on product performance. Dry granulation, as discussed above, can be accomplished using a roller compaction process. The density of the output ribbons produced from a roller compaction process is typically a critical quality attribute and can impact the particle size of milled granules, blend flowability and tabletability. Measuring the ribbon density and ensuring that the ribbon density is optimal is therefore one of the key components of the pharmaceutical product development process.

Embodiments of the present invention provide a fast, non-invasive and efficient mechanism to measure the density of a ribbon produced by a roller compactor during a dry granulation process. Further, embodiments of the present invention provide a method and apparatus to implement the test on/at-line so that the density of the ribbon can be measured in real-time as the ribbon is rolled out from in between the press rollers.

In one embodiment, terahertz time-domain spectroscopy (THz-TDS) is used to measure the refractive index of the dry granulated compact of the ribbon at one or more points on the ribbon after it is rolled out by the press rollers. As will be discussed in detail below, in one embodiment, a terahertz (THz) emitter and detector can be placed on opposite sides of the ribbon to obtain measurements as the ribbon rolls out from in between the press rollers.

Variations in refractive index can be directly related to changes in density. The density of the compact can be determined provided that the sample thickness can be measured. In one embodiment, the present invention includes laser micrometers that take on-line measurements of the ribbon thickness. The laser micrometers can be mounted adjacent (or in close proximity to) to the terahertz emitter and detector on opposite sides of the ribbon. By incorporating laser micrometers, microscopic changes in the thickness of the ribbon can be detected as the ribbon moves through the terahertz optical path. The thickness measurements from the laser micrometers in conjunction with the measurement values obtained from the terahertz spectroscopy can be used to calculate the refractive index of the ribbon material, which can, in turn, be used to determine the density of the pharmaceutical compact using a calibration equation.

Accordingly, embodiments of the present invention advantageously allow the density of a ribbon to be determined in a non-invasive and efficient manner in real time without needing to stop the roller compactor to manually obtain samples or measurements.

Figure 2:
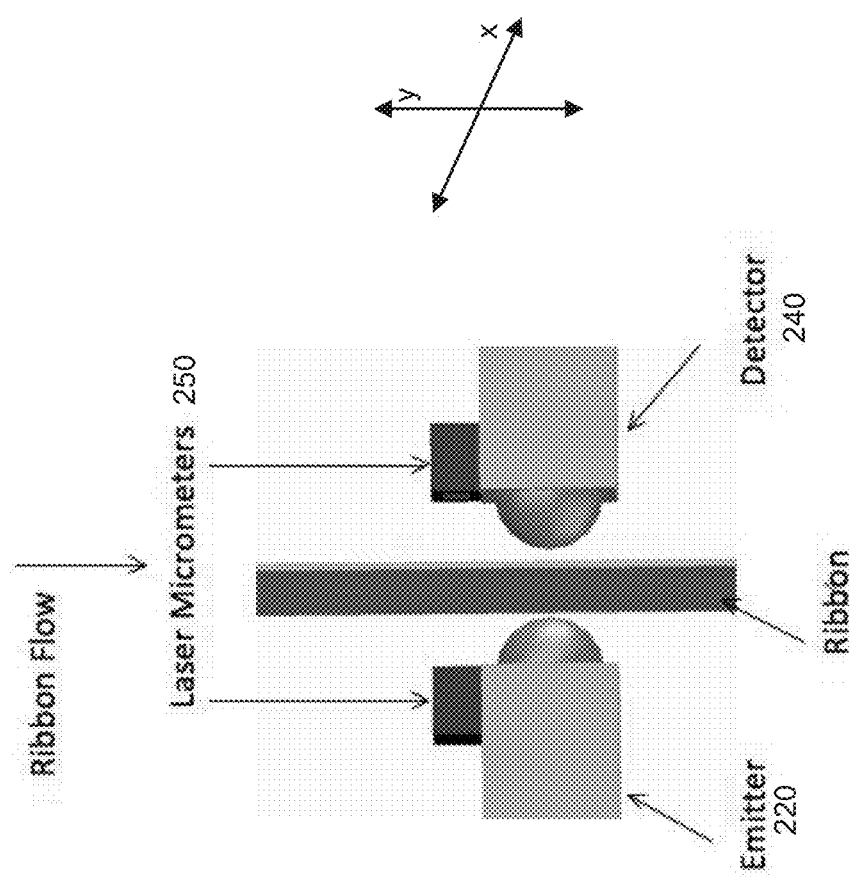
FIG. 2 is a diagram of an exemplary apparatus using terahertz spectroscopy to determine a dry granulated ribbon density in accordance with an embodiment of the present invention.

FIG. 2 is a diagram of an exemplary apparatus using terahertz spectroscopy to determine a dry granulated ribbon density in accordance with an embodiment of the present invention.

Terahertz time-domain spectroscopy is a spectroscopic technique in which the properties of a material are probed with short pulses of terahertz radiation. The generation and detection scheme is sensitive to the sample material's effect on both the amplitude and the phase of the terahertz radiation. Typically, the terahertz pulses are generated by an ultrashort pulsed laser and last only a few picoseconds. A single pulse can contain frequency components covering the terahertz range from 0.05 to 4 THz. The ultrashort width of the terahertz radiation pulses allows for measurements, e.g., thickness measurements on difficult to probe materials. Further terahertz measurements are non-contact.

Pulsed terahertz technology has the ability to measure the effective refractive indices of solid compacts. Terahertz technology is non-destructive and highly sensitive to small changes in the refractive index. As mentioned above, variations in the refractive index of a ribbon can be directly related to changes in density of the ribbon provided that the sample thickness is known. In other words, if the sample thickness of a dry granulated ribbon can be measured, then the effective refractive index of a ribbon material can be calculated. The ribbon density can then be calculated from the calibration equation using the refractive index.

Accordingly, for a terahertz measurement to be effective in an on/at-line setting to determine the density of a dry granulated ribbon, the automated test apparatus performing the terahertz measurement needs to also accurately determine the thickness of the material.

Referring now to FIG. 2, embodiments of the present invention provide a way for measuring the refractive index and the thickness for a given point or plurality of points on the ribbon in parallel. The measurements can subsequently be used to determine the density of the ribbon. As shown in the exemplary apparatus illustrated in FIG. 2, the moving pharmaceutical ribbon stream 230 passes through the gap in between a terahertz emitter 220 and detector 240 pair. In one embodiment, the ribbon is typically between 25 and 50 mm wide and approximately 1 to 2 mm thick for instance. The terahertz pulses emitted by the emitter and detected by the detector can be used to determine the refractive index of the ribbon at the point (or pixel) at which the terahertz beam is focused. In one embodiment, the size of the terahertz beam focused on the ribbon can be between 1 to 6 mm for instance.

Figure 3:
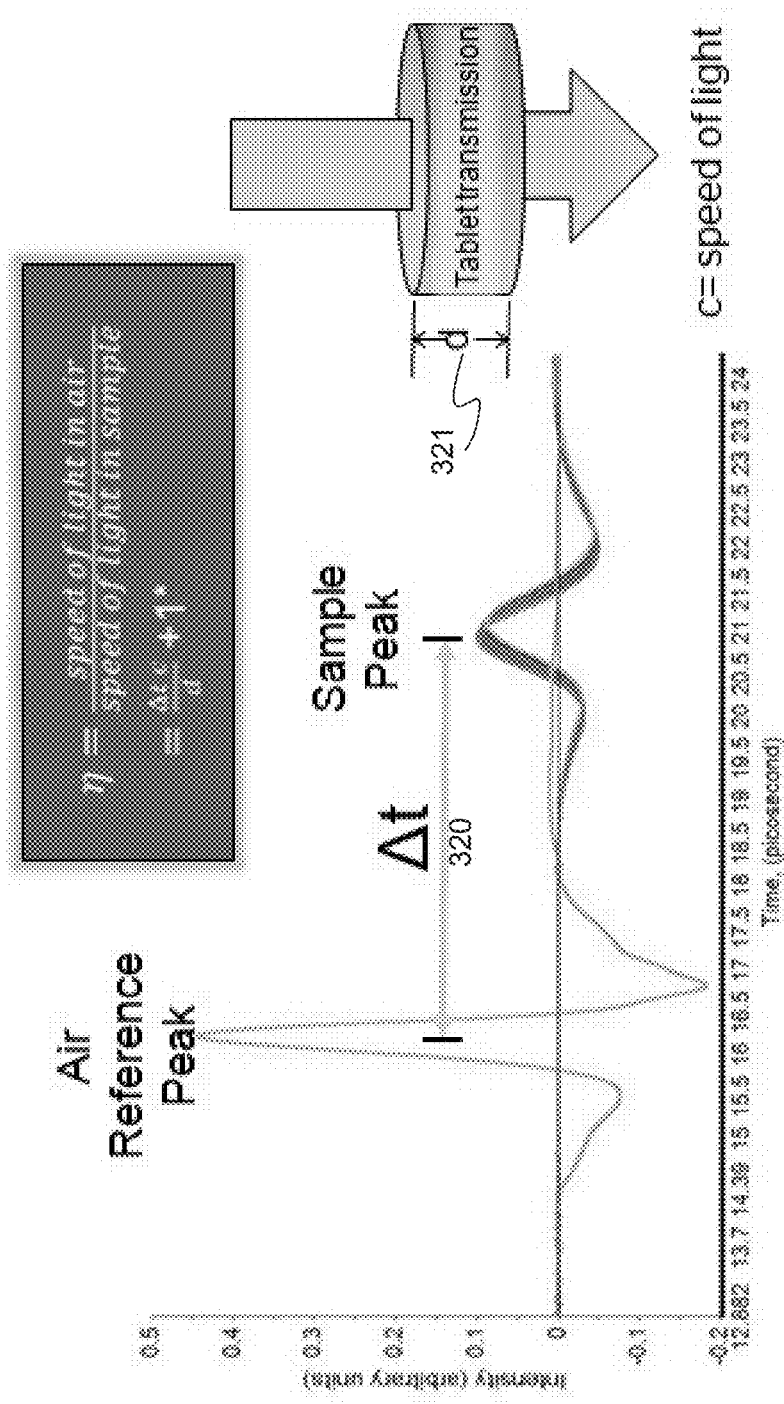
FIG. 3 illustrates the manner in which the refractive index for a sample ribbon can be determined.

FIG. 3 illustrates the manner in which the refractive index for a sample ribbon can be determined. One skilled in the art would recognize that the refractive index of the ribbon at the point measured can be obtained by evaluating the time-of-flight of the emitted terahertz pulse in air as compared to the time-of-flight through the ribbon material. The ratio of the two durations (speed of terahertz pulse in air/speed of terahertz pulse through the sample) can be used to determine the refractive index, which will be different depending on the density of the ribbon material. For a given thickness, the denser the ribbon medium the longer the radiation pulse takes to pass through it resulting in a higher refractive index value. In one embodiment, the refractive index at, for example, 0.8 THz is selected from the broadband response. At 0.8 THz, a high signal to noise ratio is obtained with minimal etalon interference.

The refractive index, in one embodiment, can be calculated using the following equation: $(\Delta t^* c)/d+1$, where $\Delta t$ 320 is the difference in the time-of-flight of the terahertz pulse passing through the sample medium with thickness d versus passing the same distance in dry air, c is the speed of light and d 321 is the thickness of the ribbon material. It should be noted that this equation is simply one exemplary method of calculating the refractive index. Other embodiments of the invention are well suited for different methods of calculating the refractive index of the ribbon material. Different embodiments, for example, may add other variables in the equation or perform different procedures in software to improve the accuracy of the measurement.

Referring back to FIG. 2, in one embodiment, the apparatus can also measure the thickness (d 321) of the ribbon at the same point as the terahertz measurement was made by taking simultaneous readings from two laser micrometers 250 mounted adjacent or in near proximity to the terahertz emitter 220 and detector 240. By incorporating a laser micrometer with each terahertz device, microscopic changes in the thickness of the ribbon can be non-invasively detected as the ribbon moves through the terahertz optical path. This provides a significant advantage over conventional methods of determining density of a roller compaction ribbon, wherein the thickness of the ribbon would need to be measured manually off-line using linear calipers or a micrometer.

In one embodiment, the apparatus illustrated in FIG. 2 can be added to a roller compactor in between the press rollers and the rotor. The measurements to determine density are, therefore, obtained in between the roller compaction and the milling processes.

In one embodiment of the present invention, the configuration illustrated in FIG. 2 can be used to determine the dynamic thickness of the ribbon sequentially with the terahertz measurement. For example, the speed of the ribbon as it is rolled out from the press rollers can be determined (through monitoring or otherwise). A time delay (or offset) can then be programmed into the ATE to ensure that the terahertz measurement is taken at the same location as the thickness reading after the ribbon is translated or offset in the y-direction. The data from the ribbon thickness can then be fed into the calculation of the effective refractive index of the ribbon at the point measured. As will be discussed further below, the ribbon density is subsequently calculated for the measured point using a calibration equation, which comprises the refractive index, and the result is recorded and displayed to the user or, alternatively, fed back to the control system to adjust the roller compaction conditions.

It should be noted that the apparatus of FIG. 2 will be incorporated within automated test equipment (ATE), wherein the ATE comprises a computing system capable of implementing embodiments of the present disclosure. The computing system can, for example, be any single or multi-processor computing device or system capable of executing computer-readable instructions. Examples of a computing system include, without limitation, workstations, laptops, client-side terminals, servers, distributed computing systems, handheld devices, or any other computing system or device. In its most basic configuration, the computing system may include at least one processor and a system memory. It may also comprise other connected peripherals, e.g., a mouse, a display, a keyboard etc.

Figure 4:
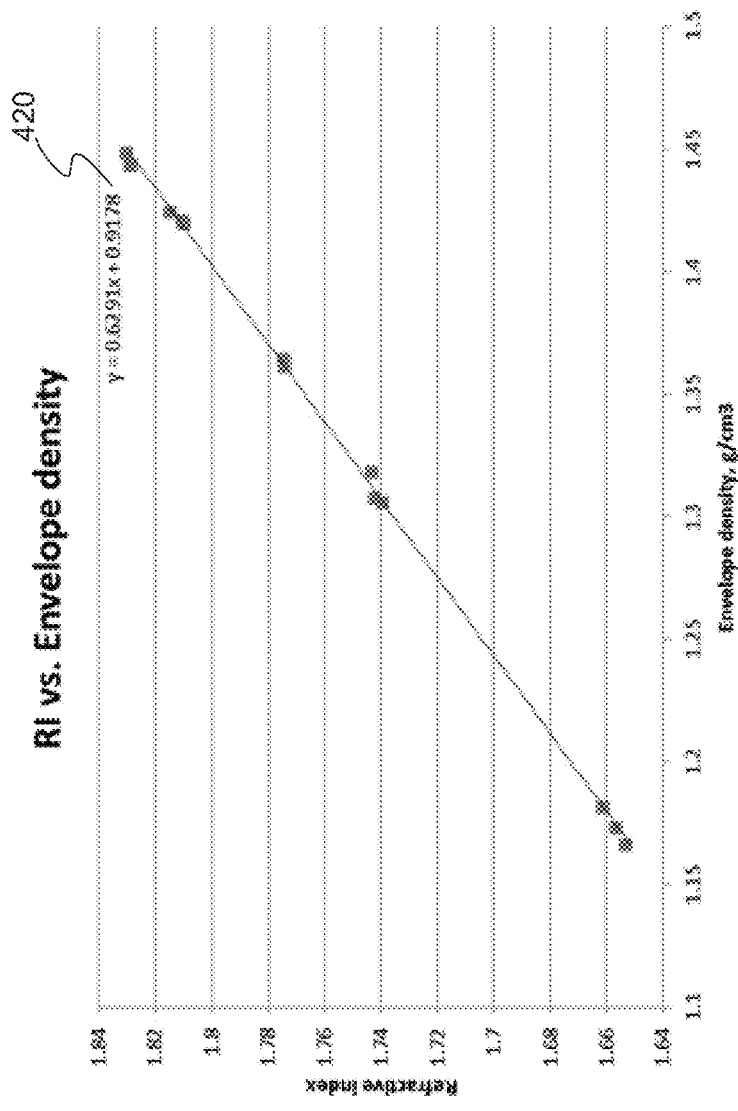
FIG. 4 illustrates the manner in which ribbon density can be determined using the refractive indices measured in accordance with one embodiment of the present invention.

FIG. 4 illustrates the manner in which ribbon density can be determined using the refractive indices measured in accordance with one embodiment of the present invention. After the refractive index measurements are made on a series of samples that span an appropriate range of densities, a graphical plot of the ribbon density versus the refractive index can be obtained for those points (by using either a predetermined equation or manual measurement to determine the density). A best fit line connecting the various points so plotted is drawn and a calibration equation (e.g. equation 420 in FIG. 4) is determined from the best fit line. Subsequently, for other refractive indices measured and calculated for the same material, the calibration equation (or graphical plot) can be used to accurately predict the density of the ribbon. Thereafter, an x-y spatial distribution of density for the ribbon compact can be determined.

In one embodiment, a larger spot size for the terahertz beam can be used. In this embodiment, the tester can be configured to take multiple thickness measurements at several points within the spot. Thereafter, an average density across the entire spot would be calculated by determining the densities for all the pixels within the spot and averaging the values so obtained.

Referring back to FIG. 2, in one embodiment of the present invention, the terahertz beam can be translated across the ribbon 230 to obtain measurements in the x-direction in addition to the y-direction. Accordingly, the cross-sectional density distribution of a ribbon can be obtained. For example, the beam can be translated across a ribbon in the x-direction to obtain measurements for a certain number of sample points before moving it in the y-direction. The ATE can also be configured so that the laser micrometers can be moved across the ribbon in the x-direction to obtain thickness measurements at the corresponding sample points after an appropriate offset or delay in the y-direction.

In one embodiment, the emitter/detector pair can be configured to move across the ribbon laterally in the x-direction beyond the width of the ribbon so that a scan can be obtained with only air in the gap. Obtaining a scan with an open beam may be necessarily periodically to recalibrate the apparatus. Also, the open beam is the reference scan that the time delta of the sample scan is measured from. In a different embodiment, an alternative approach to referencing using a dual beam is employed. The source terahertz beam in this embodiment is split two ways, wherein one path goes through the sample while the other path transmits through air bypassing the sample. Thus, the sample never needs to be displaced for referencing and a new reference is obtained in parallel with every scan, virtually eliminating the effect of drift.

In one embodiment, the emitter/detector pair may be configured to move across the ribbon laterally in the x-direction while the ribbon is also simultaneously moving in the y-direction. Because the ribbon in the y-direction simultaneously, the net result is a zig-zag sampling pattern across the ribbon.

In a different embodiment, multiple emitter/detector pairs can have a fixed configuration adjacent to each other in the x-direction in order to scan dedicated "tracks" along the ribbon flow in the y-dimension. In this embodiment, multiple laser micrometers would also be configured adjacent to respective emitter/detector pairs so that thickness measurements can be obtained at points along each corresponding track.

Figure 5:
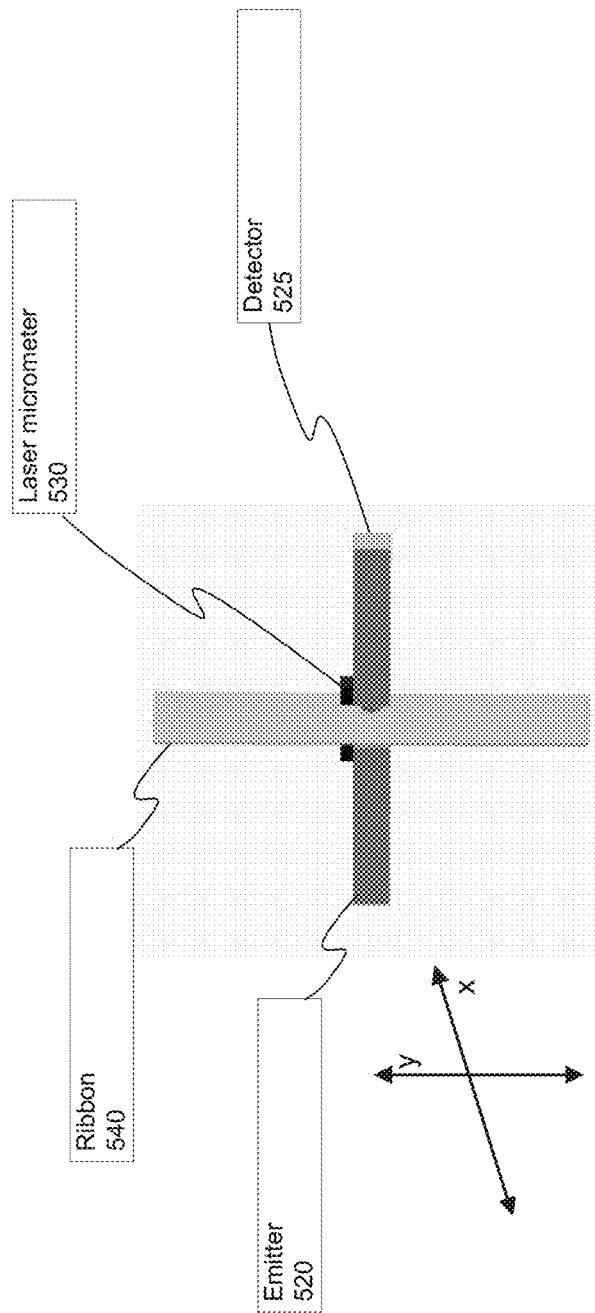
FIG. 5 is a perspective view of the apparatus illustrated in FIG. 2 in accordance with an embodiment of the present invention.

FIG. 5 is a perspective view of the apparatus illustrated in FIG. 2 in accordance with an embodiment of the present invention. The ribbon 540 passes in between the emitter 520 and detector 525 and also in between a pair of laser micrometers 530. As discussed above, the apparatus can be configured so that the thickness reading is obtained at the same point as the terahertz measurement. The thickness reading can then be used to obtain the refractive index at the measured point. The refractive index is then used to determine the density of the ribbon compact at the measured point on the ribbon.

Figure 6:
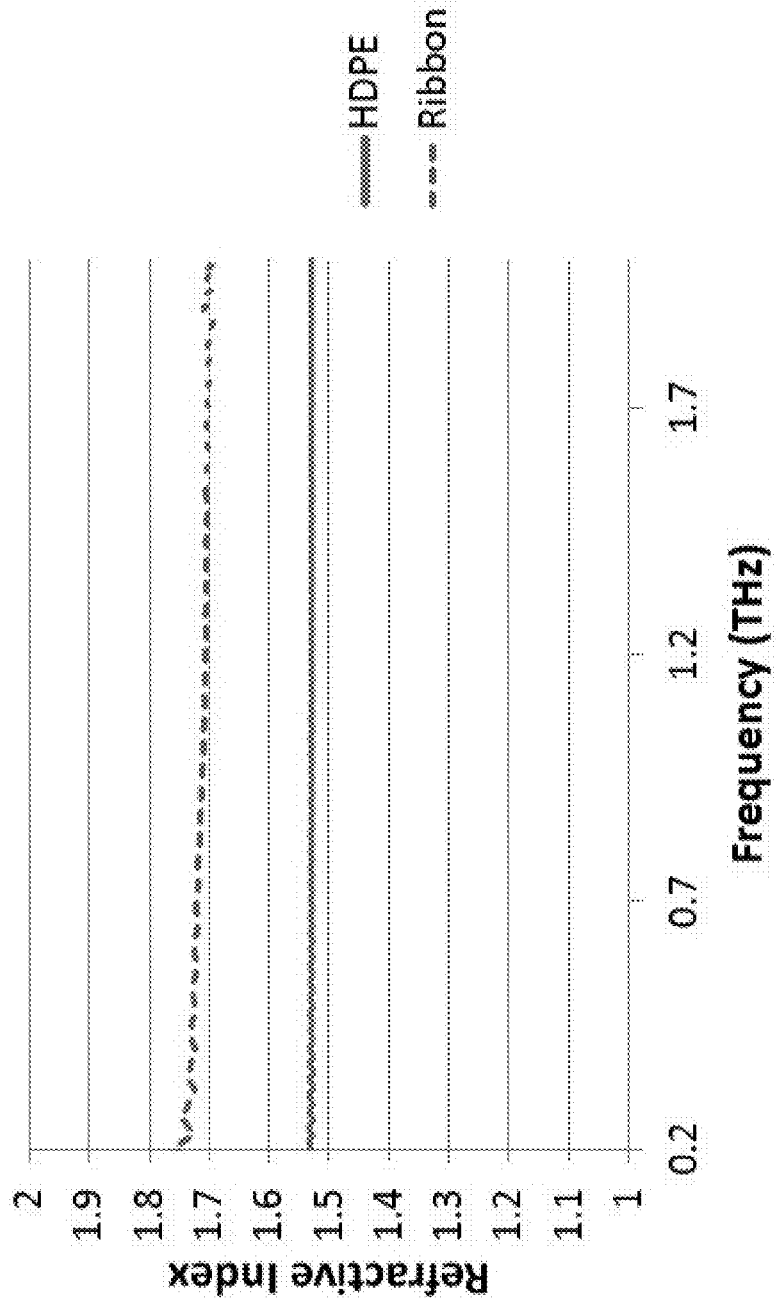
FIG. 6 illustrates a graphical plot of the refractive index measured for a standard ribbon sample in comparison with a standard reference HDPE versus the terahertz frequency in accordance with an embodiment of the present invention.

FIG. 6 illustrates a graphical plot of the refractive index measured for a standard ribbon sample in comparison with a standard reference HDPE versus the terahertz frequency in accordance with an embodiment of the present invention. FIG. 6 illustrates the accuracy of the refractive index measurement on a standard reference HDPE sample relative to a standard ribbon sample.

Figure 7:
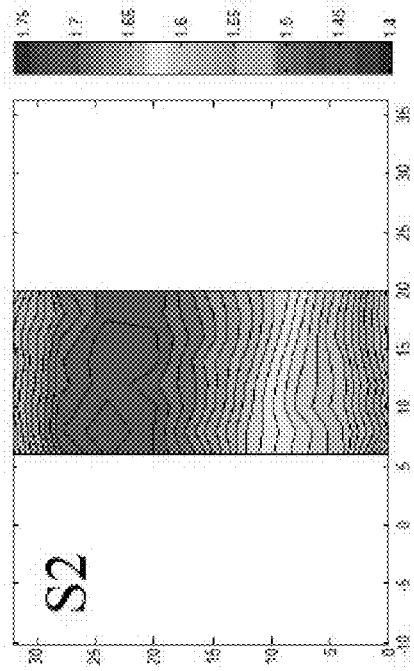
FIG. 7 illustrates refractive index contour maps that are used to display the results of tests conducted on a standard ribbon sample.
Figure 7:
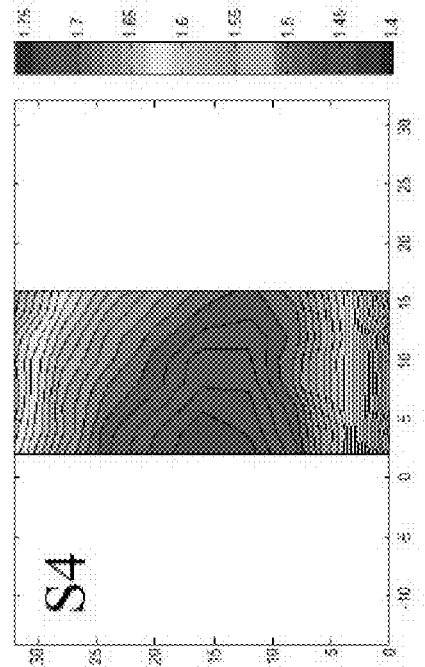
Figure 7:
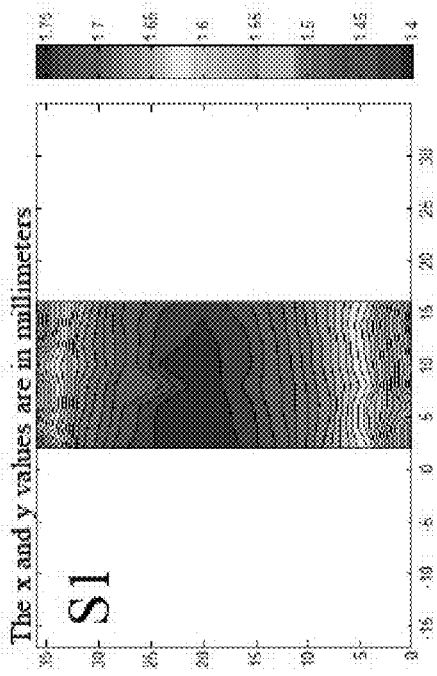
Figure 7:
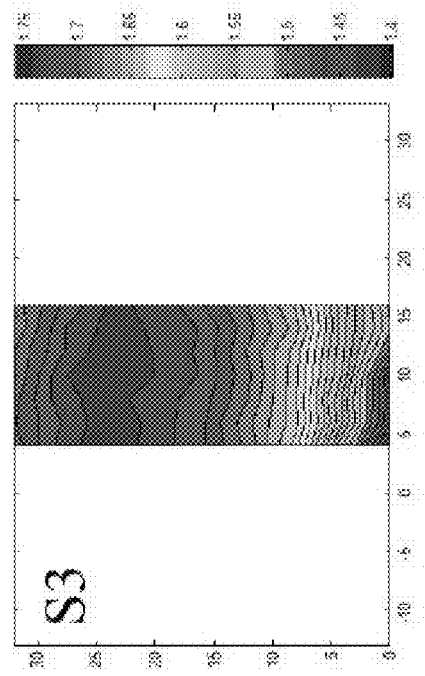

FIG. 7 illustrates refractive index contour maps that are used to display the results of tests conducted on a standard ribbon sample. In order to obtain the contour maps of FIG. 7, the ribbon was moved point-by-point in the x (2 mm steps) and y (4 mm steps) dimensions with respect to the beam. Because the ribbon was moved manually, each point or pixel was scanned for 30 seconds to collect a 4096 scan average. Measurements were recorded in a 10×8 mm grid using an alignment apparatus to control the measurement position.

While the THz beam profile used was circular, the average refractive index measured was attributed to the entire pixel. In this case, an average ribbon thickness was used for the refractive index calculation of all pixels. The raw data so collected was used to create the contour maps illustrated in FIG. 7 with the assistance of rendering software.

Figure 8:
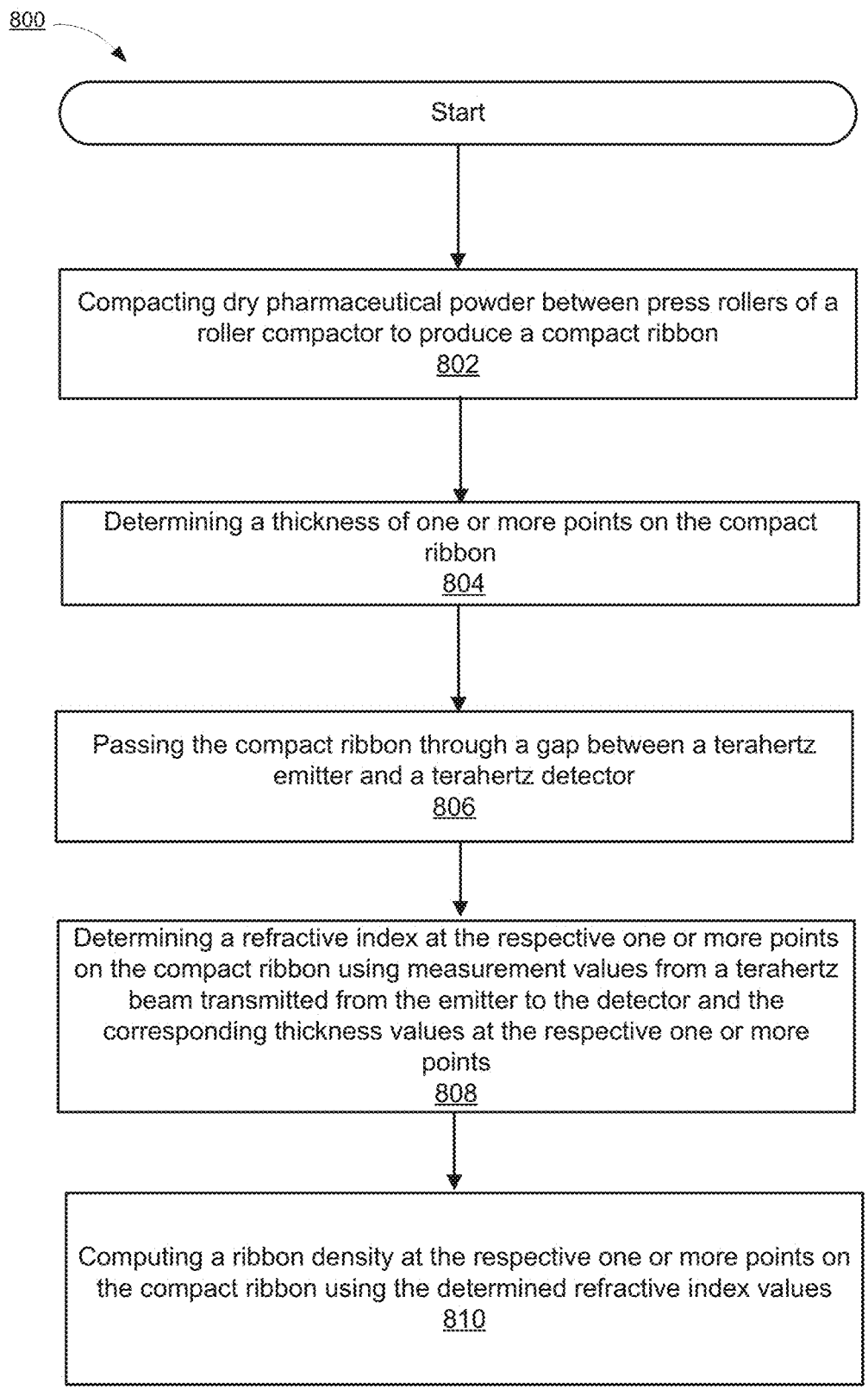
FIG. 8 depicts a flowchart of an exemplary process of determining the density of a dry granulated roller compacted ribbon in accordance with an embodiment of the present invention.

FIG. 8 depicts a flowchart 800 of an exemplary process of determining the density of a dry granulated roller compacted ribbon in accordance with an embodiment of the present invention. The present invention, however, is not limited to the description provided by flowchart 800. Rather, it will be apparent to persons skilled in the relevant art(s) from the teachings provided herein that other functional flows are within the scope and spirit of the present invention.

Flowchart 800 will be described with continued reference to exemplary embodiments described above in reference to the prior figures, though the method is not limited to those embodiments.

Referring now to FIG. 8, at step 802, a dry pharmaceutical powder is compacted between the press rollers of a roller compactor. As discussed above, dry granulation is a process in which the particles of a uniform powder mixture are forced to adhere to one another under pressure and then the resultant compact is milled into large particles that have desirable flow characteristics. When the powder blend is compacted by applying force to the powder the resulting compact is referred to as a ribbon.

At step 804, the thickness at one or more points is determined in a non-invasive manner as the ribbon rolls out of the roller compactor. In one embodiment, one or more laser micrometers are used to obtain this non-invasive measurement of thickness.

At step 806, the ribbon is rolled through a gap between a terahertz emitter and a terahertz detector as described above.

At step 808, short pulses of terahertz radiation are emitted by the emitter and detected by the detector at the same point (or points) for which thickness measurements were obtained at step 804. The time-of-flight of the pulses as it passes through the ribbon material is used in conjunction with the thickness of the compact ribbon for a given point in order to measure the refractive index at that point.

At step 810, the density of the compact ribbon at the one or more points measured is determined using the refractive index values and a calibration equation. The result can then be recorded and displayed to the user using a display on the ATE.

The process parameters and sequence of steps described and/or illustrated herein are given by way of example only. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as may be suited to the particular use contemplated.

Embodiments according to the invention are thus described. While the present disclosure has been described in particular embodiments, it should be appreciated that the invention should not be construed as limited by such embodiments, but rather construed according to the below claims.

What is claimed is:

1. A method of determining a density of a roller compacted ribbon, said method comprising:
   compacting dry pharmaceutical powder between press rollers of a roller compactor to produce a compact ribbon;
   determining a thickness at a point on said compact ribbon in a non-invasive manner after it has rolled out from in between said press rollers;
   passing said compact ribbon through a gap in between a terahertz emitter and a terahertz detector;
   determining a refractive index at said point on said compact ribbon using a measurement value from said terahertz emitter and said terahertz detector and a measured value for said thickness at said point; and computing a density of said compact ribbon at said point using a value of said refractive index and a calibration equation.

2. The method of claim 1, wherein said determining a thickness comprises measuring said thickness using a laser micrometer.

3. The method of claim 2, wherein said determining a thickness further comprises:
passing said compact ribbon through a gap between two laser micrometers; and
obtaining simultaneous readings from said two laser micrometers to determine said thickness.

4. The method of claim 1, wherein said determining a refractive index comprises:
determining a time-of-flight duration of a radiation pulse emitted by said terahertz emitter and detected by said terahertz detector for said point on said compact ribbon; and
computing said refractive index at said point using said time-of-flight duration and said thickness.

5. The method of claim 1, wherein said determining a refractive index further comprises:
translating said terahertz emitter and said terahertz detector in an x-direction to obtain refractive index values for a plurality of points on said compact ribbon, wherein the x-direction is a direction perpendicular to a direction said compact ribbon is moving.

6. The method of claim 5, wherein said determining a thickness further comprises:
translating a pair of laser micrometers in the x-direction across said compact ribbon to obtain thickness values corresponding to said plurality of points.

7. The method of claim 6, further comprising:
computing density values for said plurality of points using respective thickness and respective refractive index values corresponding to said plurality of points.

8. An apparatus for determining a density of a roller compacted ribbon, said apparatus comprising:
a roller compactor operable to compact dry pharmaceutical powder between press rollers of said roller compactor to produce a compact ribbon;
at least one laser micrometer operable to determine a thickness at a point on said compact ribbon in a non-invasive manner after it has rolled out from in between said press rollers;
a terahertz emitter operable to emit a terahertz radiation pulse through said point on said compact ribbon;
a terahertz detector operable to detect said terahertz radiation pulse;
a memory; and
a processor configured to:
determine a refractive index at said point on said compact ribbon using measured values from said terahertz emitter and said terahertz detector and a measured value for said thickness; and
compute a density of said compact ribbon at said point using a value of said refractive index and a calibration equation.

9. The apparatus of claim 8, wherein said at least one laser micrometer comprises two laser micrometers, wherein each laser micrometer is disposed on either side of said compact ribbon, and wherein thickness measurements are obtained from said two laser micrometers simultaneously.

10. The apparatus of claim 9, wherein a first of said two laser micrometers is disposed adjacent to said terahertz emitter and a second of said two laser micrometers is disposed adjacent to said terahertz detector.

11. The apparatus of claim 8, wherein said measured values from said terahertz emitter and said terahertz detector comprises a time-of-flight duration of a radiation pulse emitted by said terahertz emitter and detected by said terahertz detector for said point on said compact ribbon.

12. The apparatus of claim 8, wherein said terahertz emitter and said terahertz detector are operable to be translated in an x-direction to obtain refractive index values for a plurality of points on said compact ribbon, wherein the x-direction is a direction perpendicular to a direction said compact ribbon is moving.

13. The apparatus of claim 12, wherein said at least one laser micrometer is operable to be translated in the x-direction to obtain thickness values corresponding to said plurality of points on said compact ribbon.

14. The apparatus of claim 13, wherein said processor is further configured to compute density values for said plurality of points using respective thickness and respective refractive index values corresponding to said plurality of points.

15. A tester system comprising:
a roller compactor operable to compact dry pharmaceutical powder between press rollers of said roller compactor to produce a compact ribbon;
a plurality of laser micrometer pairs operable to determine a thickness at a plurality of points on said compact ribbon in a non-invasive manner after said compact ribbon has rolled out from in between said press rollers, wherein said plurality of laser micrometer pairs are disposed adjacent to each other in a first axis direction in order to scan dedicated tracks along a ribbon flow in a second axis direction, and wherein each pair of laser micrometers is operable to determine a thickness at a single point from said plurality of points on said compact ribbon;
a plurality of terahertz emitters, wherein each terahertz emitter is operable to emit a terahertz radiation pulse through a respective point from said plurality of points on said compact ribbon;
a plurality of terahertz detectors, wherein each terahertz detector is operable to detect said terahertz radiation pulse passing through a respective point from said plurality of points on said compact ribbon;
a memory; and
a processor configured to:
determine a refractive index at each of said plurality of points on said compact ribbon using respective measured values from said terahertz emitter and said terahertz detector and a respective measured value for said thickness; and
compute a density of said compact ribbon at each of said plurality of points using a respective value of said refractive index and a calibration equation.

16. The tester system of claim 15, wherein each pair of laser micrometers comprises two laser micrometers, wherein each laser micrometer is disposed on either side of said compact ribbon, and wherein thickness measurements are obtained from said two laser micrometers simultaneously.

17. The apparatus of claim 15, wherein measured values from each of said plurality of terahertz emitters and each of said plurality of terahertz detectors comprises a time-of-flight duration of a radiation pulse emitted by a terahertz emitter and detected by a respective terahertz detector for a respective point on said compact ribbon.

18. The apparatus of claim 15, wherein said plurality of laser micrometer pairs are disposed adjacent to said plurality of terahertz emitters and said plurality of terahertz detector pairs.

19. The apparatus of claim 15, wherein said terahertz radiation pulse is transmitted using a terahertz beam substantially in the range between 1 to 6 mm in diameter.

20. The apparatus of claim 15, wherein said processor is further configured to record a plurality of density values corresponding to measured values at said plurality of points, and wherein said tester system further comprises a display to display said plurality of density values.

\* \* \* \* \*